United States Patent
Patil et al.

(10) Patent No.: US 9,090,616 B2
(45) Date of Patent: *Jul. 28, 2015

(54) NITROGEN CONTAINING COMPOUNDS AND THEIR USE

(71) Applicants: Vijaykumar Jagdishwar Patil, Slapur (IN); Ravikumar Tadiparthi, Aurangabad (IN); Satish Birajdar, Aurangabad (IN); Sachin Bhagwat, Aurangabad (IN)

(72) Inventors: Vijaykumar Jagdishwar Patil, Slapur (IN); Ravikumar Tadiparthi, Aurangabad (IN); Satish Birajdar, Aurangabad (IN); Sachin Bhagwat, Aurangabad (IN)

(73) Assignee: Wockhardt Ltd., Bandra-Kurla Complex, Bandra East, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 14/598,959

(22) Filed: Jan. 16, 2015

(65) Prior Publication Data

US 2015/0141394 A1    May 21, 2015

Related U.S. Application Data

(60) Division of application No. 14/269,154, filed on May 4, 2014, now Pat. No. 8,969,334, which is a continuation of application No. 14/122,986, filed as application No. PCT/IB2012/054706 on Sep. 11, 2012, now Pat. No. 8,754,102.

(30) Foreign Application Priority Data

Sep. 13, 2011  (IN) ................. 2582/MUM/2011

(51) Int. Cl.
*A61K 31/546* (2006.01)
*C07D 471/04* (2006.01)
*C07D 471/08* (2006.01)
*A61K 31/439* (2006.01)
*A61K 45/06* (2006.01)
*A61K 31/407* (2006.01)
*A61K 31/437* (2006.01)

(52) U.S. Cl.
CPC ............ *C07D 471/04* (2013.01); *A61K 31/407* (2013.01); *A61K 31/437* (2013.01); *A61K 31/439* (2013.01); *A61K 31/546* (2013.01); *A61K 45/06* (2013.01); *C07D 471/08* (2013.01)

(58) Field of Classification Search
CPC .... A61K 31/456; A61K 45/06; A61K 471/08
USPC ....................................... 514/300
See application file for complete search history.

(56) References Cited

U.S. PATENT DOCUMENTS

| | | | |
|---|---|---|---|
| 7,112,592 B2 | 9/2006 | Lampilas et al. | |
| 8,754,102 B2 * | 6/2014 | Patil et al. | 514/300 |
| 8,969,334 B2 * | 3/2015 | Patil et al. | 514/203 |

FOREIGN PATENT DOCUMENTS

WO     WO2011042560 A1    4/2011

* cited by examiner

*Primary Examiner* — Niloofar Rahmani
(74) *Attorney, Agent, or Firm* — Bio Intellectual Property Services LLC (Bio IPS); O. (Sam) Zaghmout

(57) ABSTRACT

Compounds of Formula (I), their preparation and use in preventing or treating bacterial infections are disclosed.

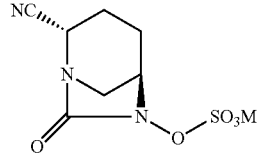

Formula (I)

9 Claims, 6 Drawing Sheets

NITROGEN CONTAINING COMPOUNDS AND THEIR USE

CROSS REFERENCE TO RELATED APPLICATIONS

This application is a division of U.S. Ser. No. 14/269,154, filed May 4, 2014, now U.S. Pat. No. 8,969,334, which is a continuation of application Ser. No. 14/122,986, filed Nov. 27, 2013, now U.S. Pat. No. 8,754,102, which is a 35 U.S.C. §371 national stage application of PCT application No. PCT/IB2012/054706, filed Sep. 11, 2012, which claims the benefit of Indian Provisional Patent Application No. 2582/MUM/2011, filed Sep. 13, 2011, all of which are incorporated herein by reference in their entirety.

FIELD OF THE INVENTION

The invention relates to nitrogen containing compounds, their preparation and their use in preventing or treating bacterial infections.

BACKGROUND OF THE INVENTION

Emergence of bacterial resistance to known antibacterial agents is becoming a major challenge in treating bacterial infections. One way forward to treat bacterial infections, and especially those caused by resistant bacteria, is to develop newer antibacterial agents that can overcome the bacterial resistance. Coates et al. (*Br. J. Pharmacol.* 2007; 152(8), 1147-1154.) have reviewed novel approaches to developing new antibiotics. However, the development of new antibacterial agents is a challenging task. For example, Gwynn et al. (*Annals of the New York Academy of Sciences*, 2010, 1213: 5-19) have reviewed the challenges in discovery of antibacterial agents.

Another approach to overcome the bacterial resistance to known antibacterial agents is to target the bacterial mechanisms, which helps it acquiring and maintaining the resistance. For example, several bacteria are known to produce enzymes (beta-lactamase enzymes) that hydrolyze the beta-lactam ring in a typical beta-lactam antibacterial agent. Once the beta-lactam ring is hydrolyzed, the antibacterial agents become ineffective against those bacteria. Bacteria are known to produce several types of beta-lactamase enzymes. Depending on their amino-acid sequence homologies, the beta-lactamase enzymes are broadly classified into four classes: A, B, C and D (Ambler R. P., *Phil. Trans. R. Soc. Lon.*, B289, 321-331, 1980). Beta-lactamase enzymes belonging to classes A, C and D use serine as the active site to facilitate catalysis, whereas those belonging to class B contain one or more metal ions (e.g. zinc ions) at the active site to facilitate the beta-lactam cleavage.

Several compounds, generally known as beta-lactamase inhibitors, are capable of inhibiting activity of one or more beta-lactamase enzymes, thereby restoring the efficacy of conventional beta-lactam antibacterial agents. Typical examples of beta-lactamase inhibitors include sulbactam, tazobactam and clavulanic acid. Drawz et al. (*Clinical Microbiology Reviews*, January 2010, Volume 23(1), p. 160-201) have reviewed the subject of beta-lactamase inhibition. U.S. Pat. No. 7,112,592 discloses several heterocyclic compounds and their use as antibacterial agents.

The inventors have surprisingly discovered nitrogen containing compounds that are useful in preventing or treating bacterial infections

SUMMARY OF THE INVENTION

Accordingly there are provided nitrogen containing compounds, methods for preparation of these compounds, pharmaceutical compositions comprising these compounds, and method for preventing or treating bacterial infection in a subject using these compounds.

In one general aspect, there are provided compounds of Formula (I):

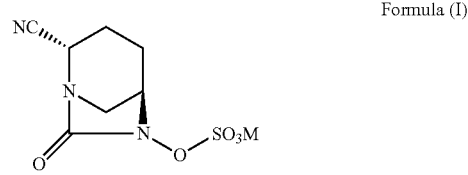

Formula (I)

or a stereoisomer or a pharmaceutically acceptable salt thereof; wherein M is a cation.

In another general aspect, there are provided pharmaceutical compositions comprising a compound of Formula (I), or a stereoisomer or a pharmaceutically acceptable salt thereof.

In another general aspect, there is provided a method for preventing or treating bacterial infection in a subject, said method comprising administering to said subject a pharmaceutically effective amount of a compound of Formula (I) or a stereoisomer or a pharmaceutically acceptable salt thereof.

In another general aspect, there is provided a method for preventing or treating a bacterial infection in a subject, said infection being caused by bacteria producing one or more beta-lactamase enzymes, wherein the method comprises administering to said subject a pharmaceutically effective amount of a compound of Formula (I) or a stereoisomer or a pharmaceutically acceptable salt thereof.

In another general aspect, there is provided a method for preventing or treating bacterial infection in a subject, said method comprising administering to said subject a pharmaceutically effective amount of a pharmaceutical composition comprising a compound of Formula (I) or a stereoisomer or a pharmaceutically acceptable salt thereof.

In yet another general aspect, there is provided a method for preventing or treating a bacterial infection in a subject, said infection being caused by bacteria producing one or more beta-lactamase enzymes, wherein the method comprises administering to said subject a pharmaceutically effective amount of a pharmaceutical composition comprising a compound of Formula (I) or a stereoisomer or a pharmaceutically acceptable salt thereof.

In another general aspect, there are provided pharmaceutical compositions comprising: (a) a compound of Formula (I), or a stereoisomer or a pharmaceutically acceptable salt thereof, and (b) at least one antibacterial agent or a pharmaceutically acceptable salt thereof.

In another general aspect, there is provided a method for preventing or treating a bacterial infection in a subject, said method comprising administering to said subject a pharmaceutically effective amount of: (a) a compound of Formula (I) or a stereoisomer or a pharmaceutically acceptable salt thereof, and (b) at least one antibacterial agent or a pharmaceutically acceptable salt thereof.

In yet another general aspect, there is provided a method for preventing or treating a bacterial infection in a subject, said infection being caused by bacteria producing one or more beta-lactamase enzymes, said method comprising administering to said subject a pharmaceutically effective amount of: (a) a compound of Formula (I) or a stereoisomer or a pharmaceutically acceptable salt thereof, and (b) at least one antibacterial agent or a pharmaceutically acceptable salt thereof.

In another general aspect, there are provided methods for increasing antibacterial effectiveness of a antibacterial agent in a subject, said method comprising co-administering said antibacterial agent or a pharmaceutically acceptable salt thereof with a pharmaceutically effective amount of a compound of Formula (I) or a stereoisomer or a pharmaceutically acceptable salt thereof.

The details of one or more embodiments of the invention are set forth in the description below. Other features, objects and advantages of the invention will be apparent from the following description including claims.

DETAILED DESCRIPTION OF THE INVENTION

Reference will now be made to the exemplary embodiments, and specific language will be used herein to describe the same. It should nevertheless be understood that no limitation of the scope of the invention is thereby intended. Alterations and further modifications of the inventive features illustrated herein, and additional applications of the principles of the invention as illustrated herein, which would occur to one skilled in the relevant art and having possession of this disclosure, are to be considered within the scope of the invention. It must be noted that, as used in this specification and the appended claims, the singular forms "a," "an," and "the" include plural referents unless the content clearly dictates otherwise. All references including patents, patent applications, and literature cited in the specification are expressly incorporated herein by reference in their entirety.

The inventors have surprisingly discovered novel nitrogen containing compounds having antibacterial properties.

The term "stereoisomers" as used herein refers to compounds that have identical chemical constitution, but differ with regard to the arrangement of their atoms or groups in space. The compounds of Formula (I) may contain asymmetric or chiral centers and, therefore, exist in different stereoisomeric forms. It is intended, unless specified otherwise, that all stereoisomeric forms of the compounds of Formula (I) as well as mixtures thereof, including racemic mixtures, form part of the present invention. In addition, the present invention embraces all geometric and positional isomers (including cis and trans-forms), as well as mixtures thereof, are embraced within the scope of the invention. In general, a reference to a compound is intended to cover it's stereoisomers and mixture of various stereoisomers.

The term "pharmaceutically acceptable salt" as used herein refers to one or more salts of a given compound which possesses the desired pharmacological activity of the free compound and which are neither biologically nor otherwise undesirable. In general, the "pharmaceutically acceptable salts" refer to salts that are suitable for use in contact with the tissues of human and animals without undue toxicity, irritation, allergic response and the like, and are commensurate with a reasonable benefit/risk ratio. Pharmaceutically acceptable salts are well known in the art. For example, S. M. Berge, et al. (*J. Pharmaceutical Sciences*, 66: 1-19, 1977), incorporated herein by reference in its entirety, describes various pharmaceutically acceptable salts in details.

In general, the compounds according to the invention contain basic (e.g. nitrogen atoms) as well as acid moieties (e.g. compounds of Formula (I) wherein M is a hydrogen). A person of skills in the art would appreciate that such compounds, therefore, can form acidic salts (formed with inorganic and/or organic acids), as well as basic salts (formed with inorganic and/or organic bases). Such salts can be prepared using procedures described in the art. For example, the basic moiety can be converted to its salt by treating a compound with a suitable amount of acid. Typical, non-limiting examples of such suitable acids include hydrochloric acid, trifluoroacetic acid, methanesulphonic acid, or the like. Alternatively, the acid moiety may be converted into its salt by treating with a suitable base. Typical non-limiting examples of such bases include sodium carbonate, sodium bicarbonate, potassium carbonate, potassium bicarbonate or the like. In case of compounds containing more than functional groups capable of being converted into salt, each such functional may be converted to salt independently. For example, in case of compounds containing two basic nitrogen atoms, one basic nitrogen can form salt with one acid while the other basic nitrogen can form salt with another acid. Some compounds according to the invention contain both, acidic as well as basic moieties, and thus can form inner salts or corresponding zwitterions. In general, all pharmaceutically acceptable salt forms of compounds of Formula (I) according to invention including acid addition salts, base addition salts, zwitterions or the like are contemplated to be within the scope of the present invention and are generically referred to as pharmaceutically acceptable salts.

The term "infection" or "bacterial infection" as used herein includes presence of bacteria, in or on a subject, which, if its growth were inhibited, would result in a benefit to the subject. As such, the term "infection" in addition to referring to the presence of bacteria also refers to normal flora, which are not desirable. The term "infection" includes infection caused by bacteria.

The term "treat", "treating" or "treatment" as used herein refers to administering a medicament, including a pharmaceutical composition, or one or more pharmaceutically active ingredients, for prophylactic and/or therapeutic purposes. The term "prophylactic treatment" refers to treating a subject who is not yet infected, but who is susceptible to, or otherwise at a risk of infection (preventing the bacterial infection). The term "therapeutic treatment" refers to administering treatment to a subject already suffering from infection. The terms "treat", "treating" or "treatment" as used herein also refer to administering compositions or one or more of pharmaceutically active ingredients discussed herein, with or without additional pharmaceutically active or inert ingredients, in order to: (i) reduce or eliminate either a bacterial infection or one or more symptoms of the bacterial infection, or (ii) retard the progression of a bacterial infection or of one or more symptoms of the bacterial infection, or (iii) reduce the severity of a bacterial infection or of one or more symptoms of the bacterial infection, or (iv) suppress the clinical manifestation of a bacterial infection, or (v) suppress the manifestation of adverse symptoms of the bacterial infection.

The term "pharmaceutically effective amount" or "therapeutically effective amount" or "effective amount" as used herein refers to an amount, which has a therapeutic effect or is the amount required to produce a therapeutic effect in a subject. For example, a therapeutically or pharmaceutically effective amount of an antibacterial agent or a pharmaceutical composition is the amount of the antibacterial agent or the pharmaceutical composition required to produce a desired therapeutic effect as may be judged by clinical trial results, model animal infection studies, and/or in vitro studies (e.g. in agar or broth media). The pharmaceutically effective amount depends on several factors, including but not limited to, the microorganism (e.g. bacteria) involved, characteristics of the subject (for example height, weight, sex, age and medical history), severity of infection and the particular type of the antibacterial agent used. For prophylactic treatments, a therapeutically or prophylactically effective amount is that amount which would be effective in preventing a microbial (e.g. bacterial) infection.

The term "administration" or "administering" includes delivery of a composition or one or more pharmaceutically active ingredients to a subject, including for example, by any appropriate methods, which serves to deliver the composition or it's active ingredients or other pharmaceutically active ingredients to the site of the infection. The method of administration may vary depending on various factors, such as for example, the components of the pharmaceutical composition or the type/nature of the pharmaceutically active or inert ingredients, the site of the potential or actual infection, the microorganism involved, severity of the infection, age and physical condition of the subject and a like. Some non-limiting examples of ways to administer a composition or a pharmaceutically active ingredient to a subject according to this invention includes oral, intravenous, topical, intrarespiratory, intraperitoneal, intramuscular, parenteral, sublingual, transdermal, intranasal, aerosol, intraocular, intratracheal, intrarectal, vaginal, gene gun, dermal patch, eye drop, ear drop or mouthwash. In case of a pharmaceutical composition comprising more than one ingredient (active or inert), one of way of administering such composition is by admixing the ingredients (e.g. in the form of a suitable unit dosage form such as tablet, capsule, solution, powder and a like) and then administering the dosage form. Alternatively, the ingredients may also be administered separately (simultaneously or one after the other) as long as these ingredients reach beneficial therapeutic levels such that the composition as a whole provides a synergistic and/or desired effect.

The term "growth" as used herein refers to a growth of one or more microorganisms and includes reproduction or population expansion of the microorganism (e.g. bacteria). The term also includes maintenance of on-going metabolic processes of a microorganism, including processes that keep the microorganism alive.

The term, "effectiveness" as used herein refers to ability of a treatment or a composition or one or more pharmaceutically active ingredients to produce a desired biological effect in a subject. For example, the term "antibacterial effectiveness" of a composition or a antibacterial agent refers to the ability of the composition or the antibacterial agent to prevent or treat the microbial (e.g. bacterial) infection in a subject.

The term "synergistic" or "synergy" as used herein refers to the interaction of two or more agents so that their combined effect is greater than their individual effects.

The term "antibacterial agent" as used herein refers to any substance, compound or a combination of substances or a combination compounds capable of: (i) inhibiting, reducing or preventing growth of bacteria; (ii) inhibiting or reducing ability of a bacteria to produce infection in a subject; or (iii) inhibiting or reducing ability of bacteria to multiply or remain infective in the environment. The term "antibacterial agent" also refers to compounds capable of decreasing infectivity or virulence of bacteria.

The term "beta-lactam antibacterial agent" as used herein refers to compounds with antibacterial properties and containing a beta-lactam nucleus in their molecular structure.

The term "beta-lactamase" as used herein refers to any enzyme or protein or any other substance that breaks down a beta-lactam ring. The term "beta-lactamase" includes enzymes that are produced by bacteria and have the ability to hydrolyze the beta-lactam ring in a beta-lactam compound, either partially or completely.

The term "beta-lactamase inhibitor" as used herein refers to a compound capable of inhibiting activity of one or more beta-lactamase enzymes, either partially or completely.

The term "pharmaceutically inert ingredient" or "carrier" or "excipient" refers to a compound or material used to facilitate administration of a compound, for example, to increase the solubility of the compound. Solid carriers include, e.g., starch, lactose, dicalcium phosphate, sucrose, and kaolin. Liquid carriers include, e.g., sterile water, saline, buffers, non-ionic surfactants, and edible oils such as oil, peanut and sesame oils. In addition, various adjuvant commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press., which is incorporated herein by reference in its entirety.

The term "subject" as used herein refers to vertebrate or invertebrate, including a mammal. The term "subject" includes human, animal, a bird, a fish, or an amphibian. Typical, non-limiting examples of a "subject" includes humans, cats, dogs, horses, sheep, bovine cows, pigs, lambs, rats, mice and guinea pigs.

The term "Ceftolozane" as used herein refers to a compound also known as CXA-101 (CAS Registry No.: 689293-68-3; Chemical Name: (6R,7R)-3-[(5-amino-4-{[(2-aminoethyl)carbamoyl]amino}-1-methyl-1H-pyrazol-2-ium-2-yl) methyl]-7-({(2Z)-2-(5-amino-1,2,4-thiadiazol-3-yl)-2-[(1-carboxy-1-methyl ethoxy)imino]acetyl}amino)-8-oxo-5-thia-1-azabicyclo[4.2.0]oct-2-ene-2-carboxylate). A reference to Ceftolozane is intended to include its pharmaceutically acceptable salts, pro-drugs, metabolites, esters, ethers, hydrates, polymorphs, solvates, complexes, enantiomers, adducts and its any other pharmaceutically acceptable derivative In one general aspect, there are provided compounds of Formula (I):

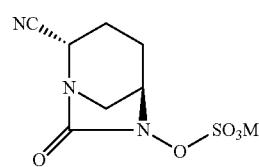

Formula (I)

or a stereoisomer or a pharmaceutically acceptable salt thereof; wherein M is a cation.

In general, the compounds of the invention can be prepared according to the general procedures given in Schemes 1 to 3. A person of skills in the art would appreciate that the described methods can be varied or optimized further to provide the desired and related compounds. In the following procedures, all variables are as defined above.

In another general aspect, there are provided pharmaceutical compositions comprising a compound of Formula (I), or a stereoisomer or a pharmaceutically acceptable salt thereof.

In another general aspect, there is provided a method for preventing or treating bacterial infection in a subject, said method comprising administering to said subject a pharmaceutically effective amount of a compound of Formula (I) or a stereoisomer or a pharmaceutically acceptable salt thereof.

In another general aspect, there is provided a method for preventing or treating a bacterial infection in a subject, said infection being caused by bacteria producing one or more beta-lactamase enzymes, wherein the method comprises administering to said subject a pharmaceutically effective amount of a compound of Formula (I) or a stereoisomer or a pharmaceutically acceptable salt thereof.

In another general aspect, there is provided a method for preventing or treating bacterial infection in a subject, said method comprising administering to said subject a pharmaceutically effective amount of a pharmaceutical composition comprising a compound of Formula (I) or a stereoisomer or a pharmaceutically acceptable salt thereof.

In yet another general aspect, there is provided a method for preventing or treating a bacterial infection in a subject, said infection being caused by bacteria producing one or more beta-lactamase enzymes, wherein the method comprises administering to said subject a pharmaceutically effective amount of a pharmaceutical composition comprising a compound of Formula (I) or a stereoisomer or a pharmaceutically acceptable salt thereof.

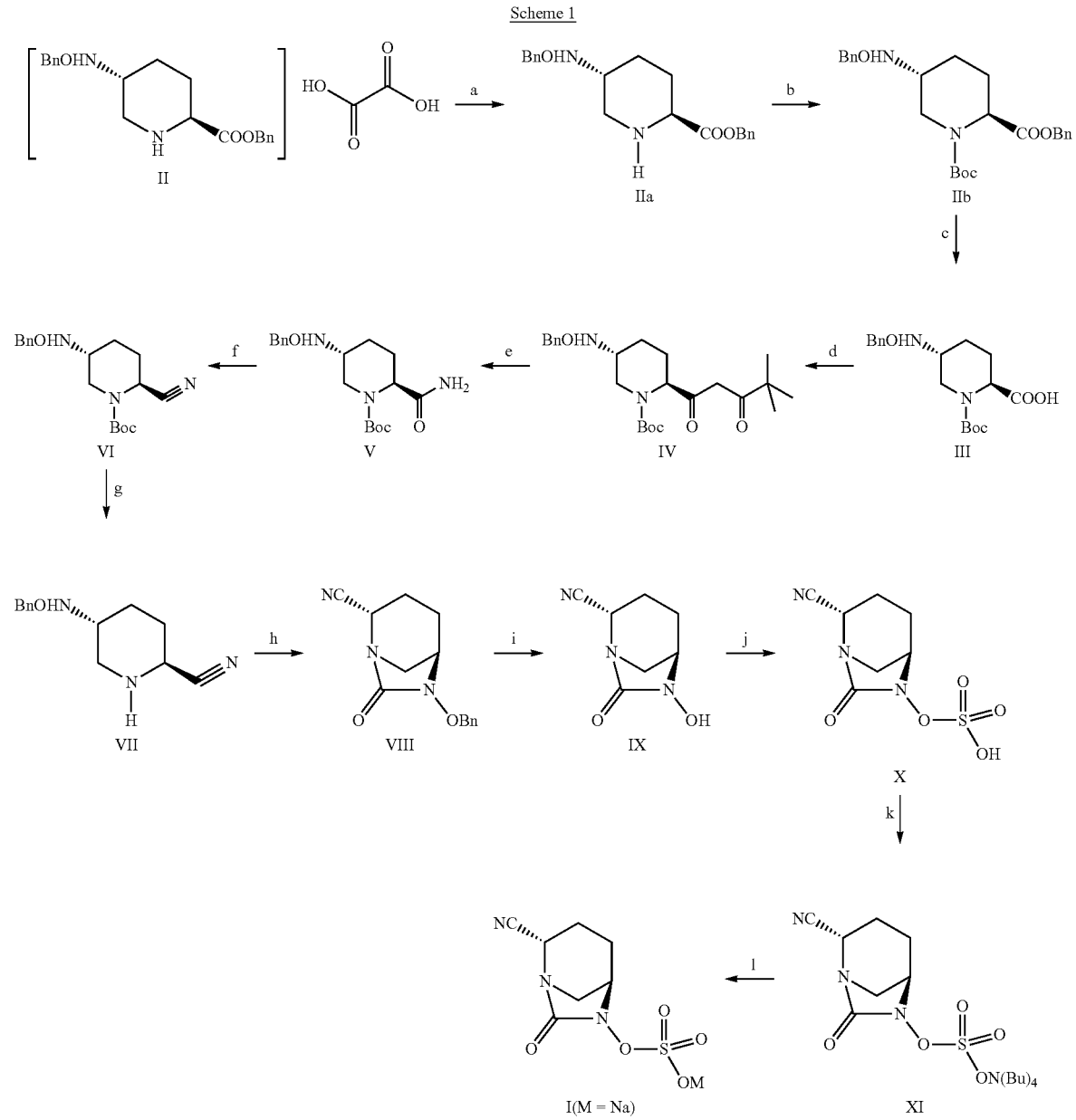

a: Base, water, RT; b:Boc-anhydride, TEA, DMAP, DCM, RT; c:LiOH, acetone;
d: Pivaloyl chloride, TEA; e. Ammonia(g); f:Trifluoroacetic anhydride, TEA, DCM
g: TFA, DCM; h: Triphosgene, TEA, DMAP, DCM; i:$H_2$, Pd/C·$SO_3$—DMF;
k: Tetrabutyl ammonium acetate, DCM; l: Dowex 500WX8 200 $Na^+$ resin Scheme 2

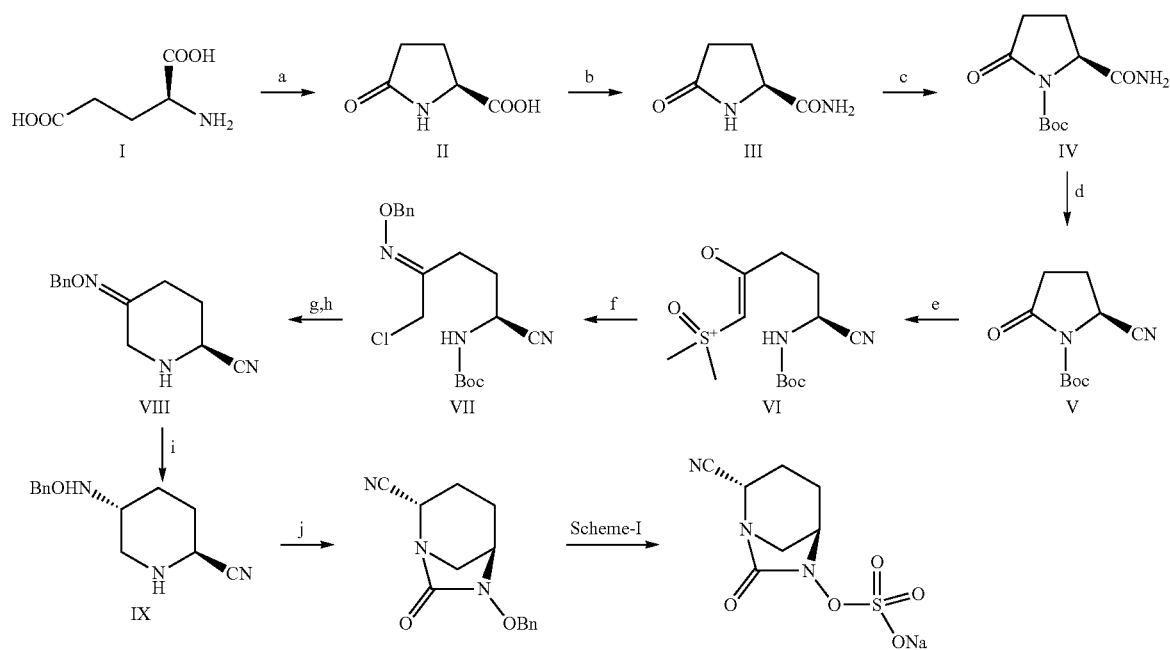

a: Water, reflux, 24 h; b:1-Hydroxybenzotriazole ammonium salt, DCC, DMF;
c: Boc-anhydride, TEA, DMAP, DCM, RT; d:Trifluoroacetic anhydride,TEA, DCM;
e: TMSOI, NaH, DMSO, THF, -10° C. 1 hr; f: O-Benzyl hydroxyl amine. HCl, EtOAc 60° C., 2.5 hr;
g: Methane sulphonic acid, ethyl acetate, 40° C.; h:.KHCO$_3$, water, 55° C.;
i: sodium triacetoxy borohydride, STABH, H$_2$SO$_4$; j: Triphosgene, TEA, DMAP, DCM;
 Scheme-1: furthur steps as depicted in scheme-1

Scheme 3

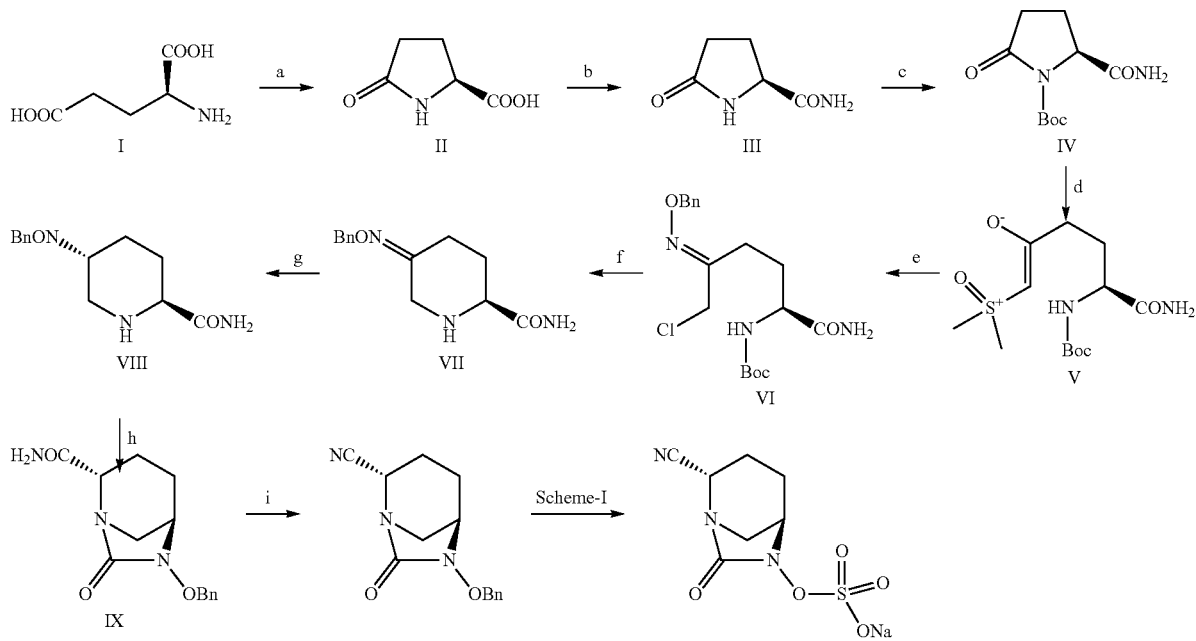

a: Water, reflux, 24 h; b:1-Hydroxybenzotriazole ammonium salt, DCC, DMF;
c: Boc-anhydride, TEA, DMAP, DCM, rt; d:TMSOI, NaH, DMSO, THF, -10° C. 1 hr;
e: O-Benzyl hydroxyl amine. HCl, EtOAc 60° C., 2.5 hr; f: Methane sulphonic acid,
 ethyl acetate, 40° C. g:.KHCO$_3$, water, 55° C.; g: sodium triacetoxy borohydride,
 STABH, H$_2$SO$_4$; h: Triphosgene, TEA, DMAP, DCM; i: Trifluoroacetic anhydride,
 TEA, DCM; Scheme-1: furthur steps as depicted in scheme-1

In some embodiments, the compound of formula (I), wherein M is sodium, was prepared using a general procedure described in Scheme 1. Typically, (S)-5-(benzyloxyamino)-piperidine-2-carboxylic acid benzyl ester oxalate salt (II) was converted into the free base by treating with a suitable base at RT to obtain the compound (IIa). This on reaction with Boc anhydride in the presence of a base and suitable catalyst like DMAP, at temperatures ranging from −5 to 40° C. was obtained the compound (IIb). This compound on hydrolysis with a base like lithium hydroxide at temp from −5 to 25° C. gave trans-5-benzyloxyamino-piperidine-1,2-dicarboxylic acid-1-tertbutyl ester compound (III).

The compound (III), was reacted with acid chloride such as pivaloyl chloride in the presence of suitable base such as N-methyl morpholine, triethylamine or diisopropyl ethylamine in a solvent such as dichloromethane, tetrahydrofuran, 1,4 dioxane or chloroform, at a temperature ranging from −5 to 35° C., for about 1 to 2 hours to provide anhydride (IV).

The anhydride (IV) was subsequently treated with ammonia gas at a temperature ranging from −50 to 5° C., for about 0.5 to 2 hours to provide amide intermediate compound (V).

Dehydration of the intermediate compound (V) was effected by treating intermediate (V) with trifluoroacetic anhydride, in a solvent such as toluene, chloroform, tetrahydrofuran, or dichloromethane, at a temperature ranging from −5 to 35° C., for about 1 to 24 hours to provide nitrile intermediate compound (VI).

The intermediate compound (VI) was deprotected to provide intermediate compound (VII), using deprotecting agent such as trifluoro acetic acid or hydrochloric acid in a solvent such as dichloromethane, chloroform, acetonitrile or water, at a temperature ranging from −25 to 50° C., for about 1 to 24 hours. The cyclization of intermediate compound (VII) was achieved by treating intermediate VII using reagent such as phosgene solution or diphosgene or triphosgene, in a solvent such as toluene, chloroform, acetonitrile, and in the presence of base such as triethyl amine or diisopropyl ethyl amine, at a temperature ranging from −5 to 50° C., for about 1 to 24 hours to provide cyclized intermediate compound (VIII).

The cyclized intermediate compound (VIII) was subjected for hydrogenolysis by using a catalyst such as 5% or 10% palladium on carbon, or 20% palladium hydroxide on carbon, in the presence of hydrogen source such as hydrogen gas, ammonium formate, formic acid or cyclohexene, in a solvent such as methanol, ethanol, methanol-dichloromethane mixture, or N,N dimethyl formamide-dichloromethane mixture at a temperature ranging from 25 to 60° C. for about 1 to 24 hours to provide N-hydroxy intermediate compound (IX).

The intermediate compound (IX) was sulfonated by reacting it with a sulfonating reagent such as pyridine sulfur trioxide complex, or N,N-dimethyl formamide sulfur trioxide complex in a solvent such as pyridine, N,N-dimethyl formamide, dichloromethane or mixture thereof at a temperature ranging from −5 to 50° C., for about 0.5 to 24 hours to provide pyridine salt of sulfonic acid (X) which subsequently was treated with tetrabutyl ammonium acetate to provide tetrabutylammonium salt of sulfonic acid intermediate compound (XI).

The compound of invention was isolated as a sodium salt by passing intermediate compound (XI) through sodium form of Dowex 50WX8 200 resin in aqueous tetrahydrofuran followed by evaporation of solvent fractions under reduced pressure to obtain the compound I, wherein M is sodium.

Alternatively this compound can be prepared by treating the compound XI with ethyl sodium hexanoate (when M=Na) in a solvent like acetone, ethyl acetate, tetrahydrofuran, ethanol, isopropanol, at temperatures from RT to 80° C.

Various polymorphs of these compounds (where M=Na) have been prepared

In another general aspect, there are provided pharmaceutical compositions comprising: (a) a compound of Formula (I), or a stereoisomer or a pharmaceutically acceptable salt thereof, and (b) at least one antibacterial agent or a pharmaceutically acceptable salt thereof.

In another general aspect, there is provided a method for preventing or treating a bacterial infection in a subject, said method comprising administering to said subject a pharmaceutically effective amount of: (a) a compound of Formula (I) or a stereoisomer or a pharmaceutically acceptable salt thereof, and (b) at least one antibacterial agent or a pharmaceutically acceptable salt thereof.

In yet another general aspect, there is provided a method for preventing or treating a bacterial infection in a subject, said infection being caused by bacteria producing one or more beta-lactamase enzymes, said method comprising administering to said subject a pharmaceutically effective amount of: (a) a compound of Formula (I) or a stereoisomer or a pharmaceutically acceptable salt thereof, and (b) at least one antibacterial agent or a pharmaceutically acceptable salt thereof.

In another general aspect, there are provided methods for increasing antibacterial effectiveness of a antibacterial agent in a subject, said method comprising co-administering said antibacterial agent or a pharmaceutically acceptable salt thereof with a pharmaceutically effective amount of a compound of Formula (I) or a stereoisomer or a pharmaceutically acceptable salt thereof.

In some embodiments, the compositions and methods according to the invention use compounds of Formula (I) or a stereoisomer or a pharmaceutically acceptable salt thereof in combination with at least one antibacterial agent. A wide variety of antibacterial agents can be used. Typical, non-limiting examples of antibacterial agents include one or more of antibacterial compounds generally classified as Aminoglycosides, Ansamycins, Carbacephems, Cephalosporins, Cephamycins, Lincosamides, Lipopeptides, Macrolides, Monobactams, Nitrofurans, Penicillins, Polypeptides, Quinolones, Sulfonamides, Tetracyclines, Oxazolidinone and the like.

Typical, non-limiting examples of Aminoglycoside antibacterial agents include Amikacin, Gentamicin, Kanamycin, Neomycin, Netilmicin, Tobramycin, Paromomycin, Arbekacin, Streptomycin, Apramycin and the like.

Typical, non-limiting examples of Ansamycin antibacterial agents include Geldanamycin, Herbimycin and the like.

Typical, non-limiting examples of Carbacephem antibacterial agents include Loracarbef and the like.

Typical, non-limiting examples of Carbapenem antibacterial agents include Ertapenem, Doripenem, Imipenem, Meropenem and the like.

Typical, non-limiting examples of Cephalosporin and Cephamycin antibacterial agents include Cefazolin, Cefacetrile, Cefadroxil, Cefalexin, Cefaloglycin, Cefalonium, Cefaloridine, Cefalotin, Cefapirin, Cefatrizine, Cefazedone, Cefazaflur, Cefradine, Cefroxadine, Ceftezole, Cefaclor, Cefamandole, Cefminox, Cefonicid, Ceforanide, Cefotiam, Cefprozil, Cefbuperazone, Cefuroxime, Cefuzonam, Cephamycin, Cefoxitin, Cefotetan, Cefmetazole, Carbacephem, Cefixime, Ceftazidime, Ceftriaxone, Cefcapene, Cefdaloxime, Cefdinir, Cefditoren, Cefetamet, Cefmenoxime, Cefodizime, Cefoperazone, Cefotaxime, Cefpimizole, Cefpiramide, Cefpodoxime, Cefsulodin, Cefteram, Ceftibuten, Ceftiolene, Ceftizoxime, Oxacephem, Cefepime, Cefozopran, Cefpirome, Cefquinome, Ceftobiprole, Ceftiofur, Cefquinome, Cefovecin, CXA-101, Ceftaroline, Ceftobiprole etc.

Typical, non-limiting examples of Lincosamide antibacterial agents include Clindamycin, Lincomycin and the like.

Typical, non-limiting examples of Macrolide antibacterial agents include Azithromycin, Clarithromycin, Dirithromycin, Erythromycin, Roxithromycin, Troleandomycin, Telithromycin, Spectinomycin and the like.

Typical, non-limiting examples of Monobactam antibacterial agents include Aztreonam and the like.

Typical, non-limiting examples of Nitrofuran antibacterial agents include Furazolidone, Nitrofurantoin and the like.

Typical, non-limiting examples of Penicillin antibacterial agents include Amoxicillin, Ampicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Temocillin, Ticarcillin and the like.

Typical, non-limiting examples of Polypeptide antibacterial agents include Bacitracin, Colistin, Polymyxin B and the like.

Typical, non-limiting examples of Quinolone antibacterial agents include Ciprofloxacin, Enoxacin, Gatifloxacin, Levofloxacin, Lomefloxacin, Moxifloxacin, Nalidixic acid, Norfloxacin, Ofloxacin, Trovafloxacin, Grepafloxacin, Sparfloxacin, Temafloxacin and the like.

Typical, non-limiting examples of Sulfonamide antibacterial agents include Mafenide, Sulfonamidochrysoidine, Sulfacetamide, Sulfadiazine, Sulfamethizole, Sulfamethoxazole, Sulfasalazine, Sulfisoxazole, Trimethoprim and the like.

Typical, non-limiting examples of Tetracycline antibacterial agents include Demeclocycline, Doxycycline, Minocycline, Oxytetracycline, Tetracycline, Tigecycline and the like.

Typical, non-limiting examples of Oxazolidinone antibacterial agents include Linezolid, Ranbezolid, Torezolid, Radezolid etc.

The pharmaceutical compositions according to the invention may include one or more pharmaceutically acceptable carriers or excipients or the like, Typical, non-limiting examples of such carriers or excipient include mannitol, lactose, starch, magnesium stearate, sodium saccharine, talcum, cellulose, sodium crosscarmellose, glucose, gelatin, sucrose, magnesium carbonate, wetting agents, emulsifying agents, solubilizing agents, pH buffering agents, lubricants, stabilizing agents, binding agents etc.

The pharmaceutical compositions according to this invention can exist in various forms. In some embodiments, the pharmaceutical composition is in the form of a powder or a solution. In some other embodiments, the pharmaceutical compositions according to the invention are in the form of a powder that can be reconstituted by addition of a compatible reconstitution diluent prior to parenteral administration. Non-limiting example of such a compatible reconstitution diluent includes water.

In some other embodiments, the pharmaceutical compositions according to the invention are in the form of a frozen composition that can be diluted with a compatible diluent prior to parenteral administration.

In some other embodiments, the pharmaceutical compositions according to the invention are in the form ready to use for parenteral administration.

In the methods according to the invention, the pharmaceutical composition and/or other pharmaceutically active ingredients disclosed herein may be administered by any appropriate method, which serves to deliver the composition or its constituents or the active ingredients to the desired site. The method of administration can vary depending on various factors, such as for example, the components of the pharmaceutical composition and nature of the active ingredients, the site of the potential or actual infection, the microorganism (e.g. bacteria) involved, severity of infection, age and physical condition of the subject. Some non-limiting examples of administering the composition to a subject according to this invention include oral, intravenous, topical, intrarespiratory, intraperitoneal, intramuscular, parenteral, sublingual, transdermal, intranasal, aerosol, intraocular, intratracheal, intrarectal, vaginal, gene gun, dermal patch, eye drop, ear drop or mouthwash.

The compositions according to the invention can be formulated into various dosage forms wherein the active ingredients and/or excipients may be present either together (e.g. as an admixture) or as separate components. When the various ingredients in the composition are formulated as a mixture, such composition can be delivered by administering such a mixture. The composition or dosage form wherein the ingredients do not come as a mixture, but come as separate components, such composition/dosage form may be administered in several ways. In one possible way, the ingredients may be mixed in the desired proportions and the mixture is then administered as required. Alternatively, the components or the ingredients (active or inert) may be separately administered (simultaneously or one after the other) in appropriate proportion so as to achieve the same or equivalent therapeutic level or effect as would have been achieved by administration of the equivalent mixture.

Similarly, in the methods according to the invention, the active ingredients disclosed herein may be administered to a subject in several ways depending on the requirements. In some embodiments, the active ingredients are admixed in appropriate amounts and then the admixture is administered to a subject. In some other embodiments, the active ingredients are administered separately. Since the invention contemplates that the active ingredients agents may be administered separately, the invention further provides for combining separate pharmaceutical compositions in kit form. The kit may comprise one or more separate pharmaceutical compositions, each comprising one or more active ingredients. Each of such separate compositions may be present in a separate container such as a bottle, vial, syringes, boxes, bags, and the like. Typically, the kit comprises directions for the administration of the separate components. The kit form is particularly advantageous when the separate components are preferably administered in different dosage forms (e.g., oral and parenteral) ore are administered at different dosage intervals. When the active ingredients are administered separately, they may be administered simultaneously or sequentially.

The pharmaceutical composition or the active ingredients according to the present invention may be formulated into a variety of dosage forms. Typical, non-limiting examples of dosage forms include solid, semi-solid, liquid and aerosol dosage forms; such as tablets, capsules, powders, solutions, suspensions, suppositories, aerosols, granules, emulsions, syrups, elixirs and a like.

In general, the pharmaceutical compositions and method disclosed herein are useful in preventing or treating bacterial infections. Advantageously, the compositions and methods disclosed herein are also effective in preventing or treating infections caused by bacteria that are considered be less or not susceptible to one or more of known antibacterial agents or their known compositions. Some non-limiting examples of such bacteria known to have developed resistance to various antibacterial agents include *Acinetobacter, E. coli, Pseudomonas aeruginosa, Staphylococcus aureus, Entero-* bacter, *Klebsiella, Citrobacter* and a like. Other non-limiting examples of infections that may be prevented or treated using the compositions and/or methods of the invention include: skin and soft tissue infections, febrile neutropenia, urinary tract infection, intraabdominal infections, respiratory tract infections, pneumonia (nosocomial), bacteremia meningitis, surgical, infections etc.

Surprisingly, the compounds, compositions and methods according to the invention are also effective in preventing or treating bacterial infections that are caused by bacteria producing one or more beta-lactamase enzymes. The ability of compositions and methods according to the present invention to treat such resistant bacteria with typical beta-lactam antibiotics represents a significant improvement in the art.

In general, the compounds of Formula (I) or a stereoisomer or pharmaceutically acceptable salt thereof according to invention are also useful in increasing antibacterial effectiveness of a antibacterial agent in a subject. The antibacterial effectiveness one or more antibacterial agents may increased, for example, by co-administering said antibacterial agent or a pharmaceutically acceptable salt thereof with a pharmaceutically effective amount of a compound of Formula (I) or a stereoisomer or a pharmaceutically acceptable salt thereof according to the invention.

It will be readily apparent to one skilled in the art that varying substitutions and modifications may be made to the invention disclosed herein without departing from the scope and spirit of the invention. For example, those skilled in the art will recognize that the invention may be practiced using a variety of different compounds within the described generic descriptions.

EXAMPLES

The following examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

Preparation of Sodium salt of trans-7-oxo-6-(sulphoxy)-1,6-diazabicyclo[3.2.1]-octane-2-carbonitrile
I Step 1: Preparation of freebase and -Boc protection

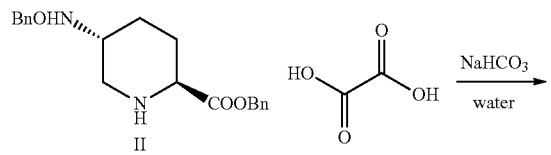

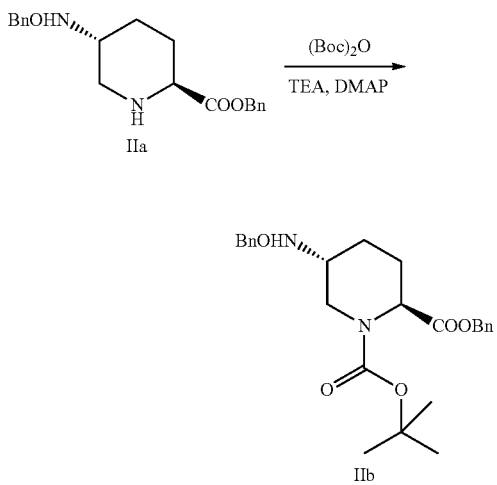

The oxalate salt II (30 g, 0.0697 moles) was partitioned between water (300 ml), and ethyl acetate (300 ml) followed by addition of sodium bicarbonate (11.7 gm, 0.139 moles) under stirring. After 1hr the organic layer was separated and the aqueous layer was extracted with ethyl acetate (150 ml). The combined organic layer was washed with water (150 ml) then brine (150 ml), dried (over $Na_2SO_4$) and the solvent evaporated under reduced pressure to obtain the free base IIa, 24 gm.

To a cooled (5-10° C. solution of the free base (24 g, 0.0705 moles) in DCM (240 ml) were added triethylamine (19.68 ml, 0.141 moles), Boc anhydride (17.8 ml, 0.0775 moles) under stirring. After 30 min. was added DMAP (0.86 gm, 0.00705 moles) and the resulting solution was allowed to warm to room temperature and stirred for a further 16 hrs. The reaction mixture was diluted with saturated aqueous ammonium chloride solution (10 ml), stirred well and the DCM layer was separated, washed with water (10 ml) and finally with brine (10 ml). The solvent was evaporated under reduced pressure and the residue chromatographed on a column of silica gel (60-120 mesh). Elution with mixtures of ethyl acetate: hexane 25-50% and concentration of the combined fractions gave the product as a colorless oil, 25 gm (yield: 80%).

MS: 439 [M+]; MF: $C_{26}H_{33}NO_5$; MW: 439.

Step 2: Hydrolysis of Benzyl ester

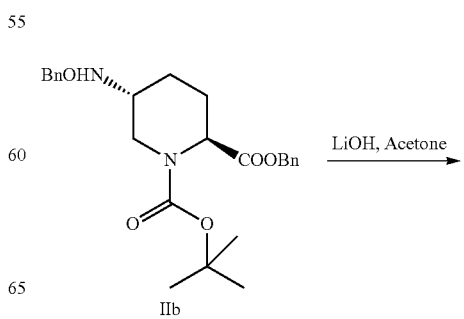

-continued

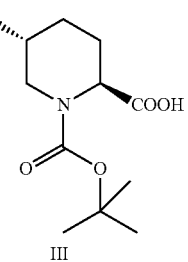
III

To a solution of the compound IIb (25 gm, 0.0567 moles) in acetone (500 ml), at 0° C., was added lithium hydroxide solution (3.81 gm, 0.0908 moles in mixture of 228.6 ml water and 76.2 ml acetone) drop-wise under vigorous stirring. The reaction mixture was allowed to warm to RT and stirring continued further for 5 hrs. The resulting mixture was cooled to 0° C. and pH adjusted to 8 to 8.5 with 2N HCl (~10 ml). The reaction mixture was diluted with brine (75 ml) and toluene (250 ml) under stirring, and after 10 minutes the organic layer was separated. The aqueous layer was re-extracted with toluene (2×120 ml). The aqueous layer was acidified to pH 3-4 by using 2N HCl and the solution extracted with ethyl acetate (3×200 ml). The combined organic layer was washed with water (200 ml), and brine (200 ml), dried (over $Na_2SO_4$) and the solvent evaporated under reduced pressure to obtain the product as a thick oil, 21 g, (quantitative yield).

MS: 349 ($M^+$); MF: $C_{19}H_{27}NO_5$; MW: 349

Step 3: Conversion of Acid to Amide

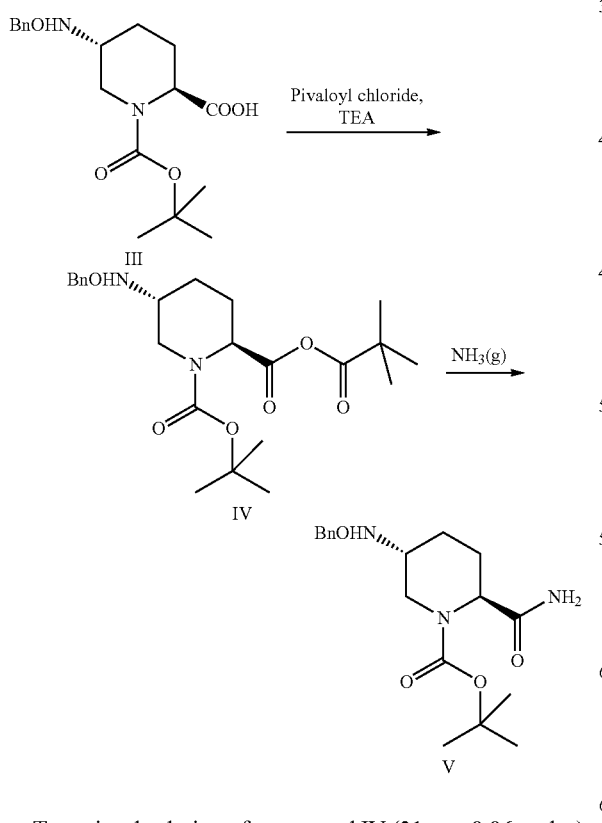

To a stirred solution of compound IV (21 gm, 0.06 moles) in DCM (210 ml) at 0° C. was added TEA (25.12 ml, 0.18 moles) followed by slow addition of Pivaloyl chloride (11.07 ml, 0.09 moles). The resulting mixture was stirred further for 1.5 hrs. The reaction mixture was cooled to −40° C. and dry ammonia gas was bubbled through the reaction mixture for 30 min. The reaction mixture was allowed to warm to RT and the suspended white solid was filtered off. The solvent was evaporated under reduced pressure and the residue chromatographed on a column of silica gel (60-120 mesh). Elution with a mixture of acetone: hexane system (1:4) and concentration of the combined solvents gave the product, as thick oil, 10.2 gm (yield: 49%)

MS: 348[$M^+$]; MF: $C_{19}H_{28}N_2O_4$; MW: 348.

Step 4: Conversion of Amide to Cyano

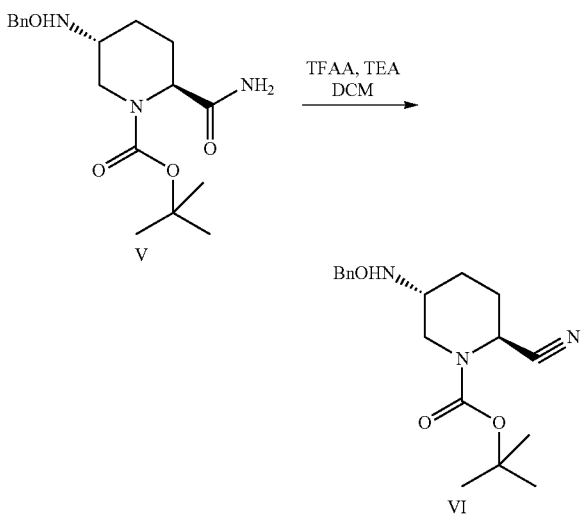

To a cooled (0° C.) and stirred solution of compound VI (10.2 gm, 0.0286 moles) in DCM (306 ml) was added Triethylamine (17.99 ml, 1.289 moles) and followed by the slow addition of Trifluoro acetic anhydride (12.08 gm, 0.0573 moles). The resulting solution was allowed to warm to RT and stirred for a further 6 h. The reaction mixture was washed water (3*100 ml), Saturated ammonium chloride solution (100 ml) and brine (100 ml). The organic layer was dried ($Na_2SO_4$) and the solvent evaporated under reduced pressure. The residue was chromatographed on a column of silica gel (60-120 mesh) using a mixture of Acetone: Hexane (1:19). Concentration of the combined fractions gave the product, as a white solid, 9.7 gm (yield—quantitative).

MS: 331 ($M^+$); MF: $C_{18}H_{25}N_3O_3$; MW: 331

Step 5: Deprotection of Cyano

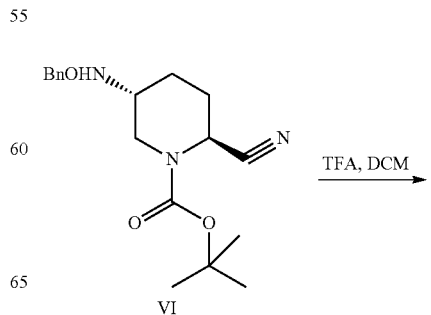
VI

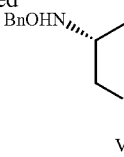

VII

To a chilled (−15° C.) and stirred solution of compound VII (6 gm) in DCM (150 ml) was added Trifluoro acetic acid (12 ml) and the mixture was allowed to warm to RT. The reaction mixture was stirred for a further 4 hrs. The solvent was evaporated under reduced pressure at 40±5° C. and the residue diluted with aqueous sat. sodium bicarbonate solution (60 ml) and the mixture extracted with DCM (2×60 ml). The combined extracts were washed with water (60 ml), dried (over sodium sulphate) and evaporated under reduced pressure at 35±5° C. to obtain 4.2 gm of compound VIII.

Step 6: Formation of Bi-Cyclic Compound

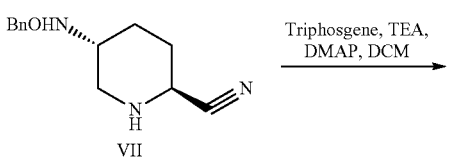

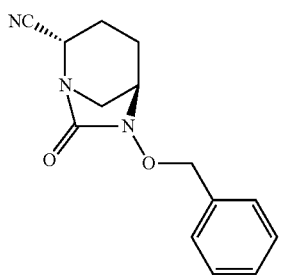

VIII

To the cooled (0-5° C.) and stirred solution of compound VIII (4.2 gm) in acetonitrile (63 ml) was added triethyl amine (5.28 ml) followed by a slow addition of a solution of Triphosgene (1.9 gm) in Acetonitrile (16.8 ml). Stirring was further continued for 30 min. followed by addition of Dimethyl amino pyridine (0.178 gm). The reaction mixture was allowed to warm to RT and stirred for further 16 hrs. A aqueous sat. solution of sodium bicarbonate (33.6 ml) was added to the reaction mixture and the resulting mixture stirred for 30 min. The mixture was concentrated to $\frac{1}{3}^{rd}$ volume under reduced pressure. The residue was diluted with water (42 ml) and the resulting mixture extracted with DCM (2×42 ml). The solvent was evaporated under reduced pressure and the residue purified over a column of silica-gel (60-120 mesh). Elution with a 1:4 mixture of acetone: hexane and concentration of the combined fractions gave the product as white solid, 2.3 g (yield: 48%).

MS: 314 (M+); MF; $C_{16}H_{18}N_4O_3$; MW; 314

Step 7: Synthesis of TBA Sulfate Salt

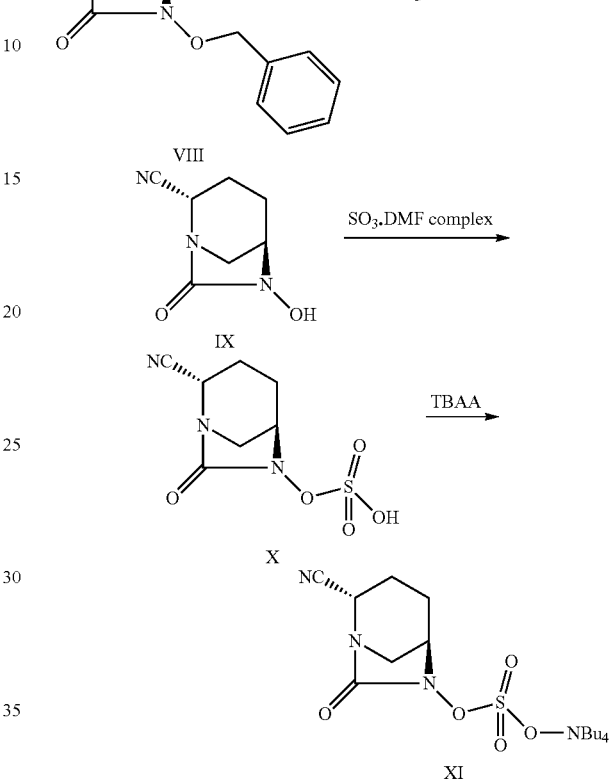

To a solution of benzyl compound VIII (6 gm, 0.0233 mol) in a 1:1 mixture of DCM (30 ml) & DMF (30 ml), was added 1.5 gm of dry 10% Palladium charcoal and the mixture was hydrogenated under 3 kg Hydrogen pressure for 3 hour at 25-30° C. The reaction mixture was filtered through micron filter to remove catalyst and the filtrate concentrated under reduced pressure to obtain the debenzylated compound IX.

The debenzylated compound (IX) was dissolved in N,N'-Dimethyl formamide (30 ml) under argon atmosphere and the solution cooled to 0° C. DMF: $SO_3$ (4.26 gm, 0.0278 mol) was added to the cooled solution and the stirring continued further for 30 min at 0° C. The mixture was then allowed to warm to RT and stirred for 1 hour. TLC showed complete conversion of N-Hydroxy compound to product X.

The solution containing the sulfate (X) was re-cooled to 0° C. and a solution of Tetra butyl ammonium acetate (9 gm, 0.0301 mol dissolved in 30 ml water) was added to it. The reaction mixture was allowed to warm to 25° C. and stirred for 1 hour. The volatiles were removed under reduced pressure and residue was co-evaporated with 2×50 ml Xylene to remove traces of N,N'-Dimethyl formamide. The residue was partitioned between a 1:1 mixture of water and dichloromethane (120 ml). The aqueous layer was re-extracted with dichloromethane (30 ml). The combined organic extracts were washed with water (2×30 ml), brine (30 ml). And dried over $Na_2SO_4$ and the solvent evaporated under reduced pressure to obtain the crude TBA sulfate (5.2 gm). Crude compound was triturated with hexane (2×30 ml) & dried on rotavapor under 4 mmHg pressure to obtain the TBA salt (XI), 5.0 g, yield-44%.

Mass: 246 (M-H) of sulfate M.W: 488, M.F: $C_{23}H_{44}N_4O_5S$.

Step 8: Synthesis of Sodium salt of trans-7-oxo-6-(sulphoxy)-1,6-diazabicyclo[3.2.1]-octane-2-carbonitrile I

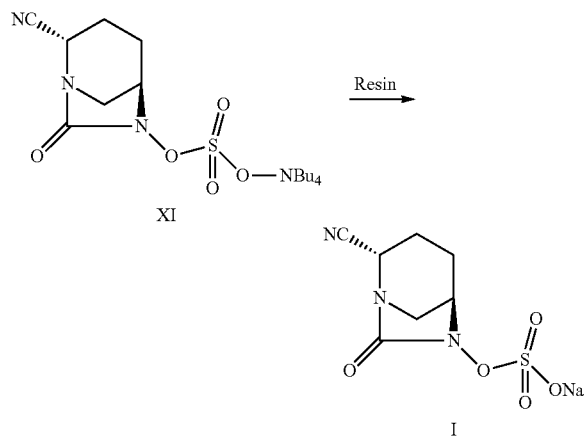

The TBA sulfate (4.4 g, 0.009 mol) was dissolved in 5% THF in water (2 ml) and the solution was passed through column (45 cm length and 2.0 cm diameter) packed with Dowex 50WX8 200 Na⁺ resin. The column was eluted with 5% THF-water mixture (100 ml). The combined fractions were evaporated under reduced pressure (4 mmHg) to obtain the product as white semi-solid, 1.5 gm, yield: 62%.

MS: 246 (M-H) of sulfate; M.W.: 269; M.F.: $C_7H_8N_3O_5SNa$, $^1$H NMR (DMSO): δ 4.54 (d, 1H), 4.06 (s, 1H), 3.22 (m, 2H), 1.96 (m, 2H), 1.84 (m, 2H).

The X-ray powder diffraction pattern of various polymorphs of this compound, when crystallized from different solvents is given in FIG. 1 to 6 (description given below)

BIOLOGICAL ACTIVITY DATA

Figure 1:
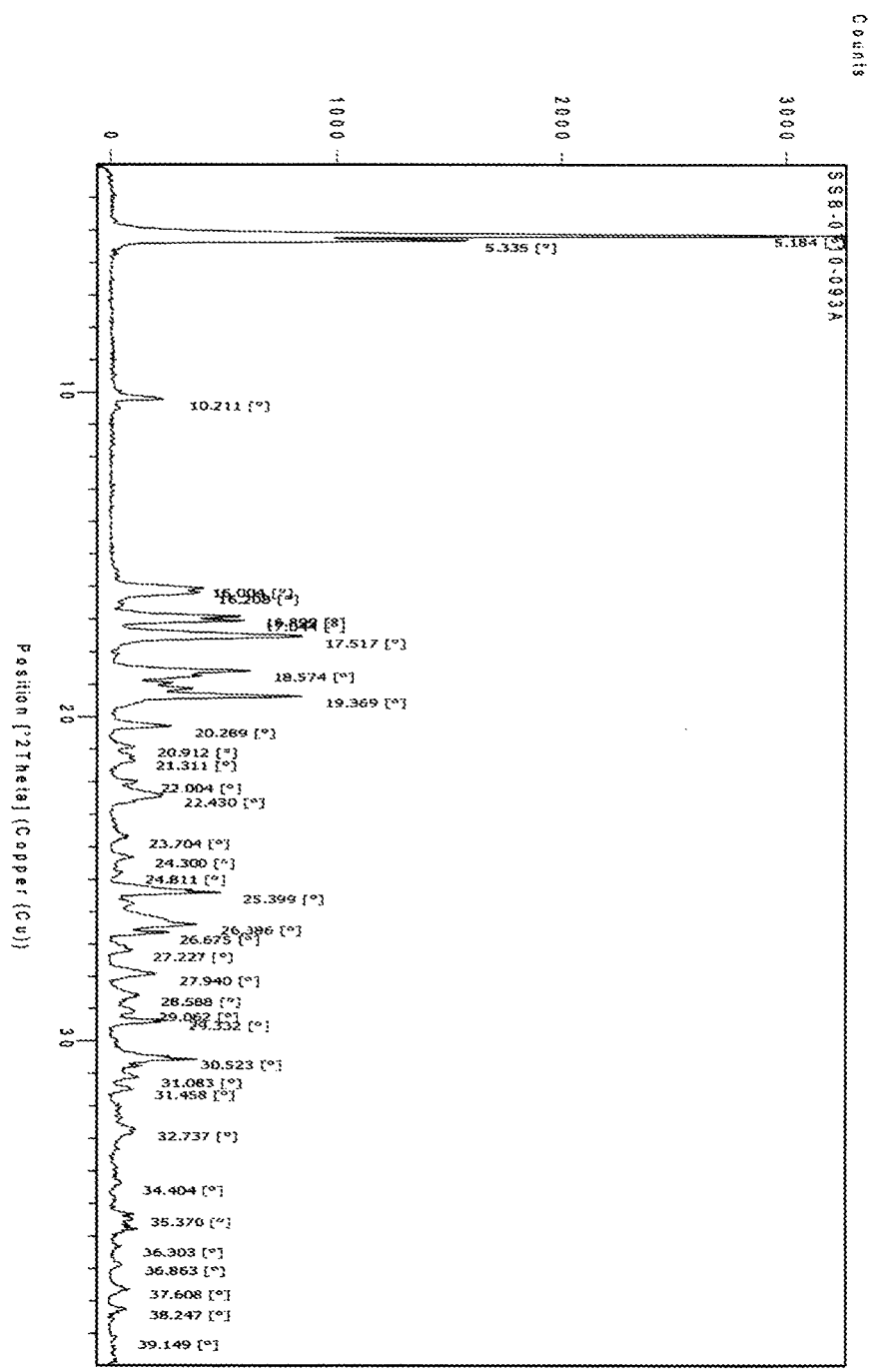
FIG. 1 is X-ray diffraction pattern of Polymorph I of Sodium salt of trans-7-oxo-6-(sulphoxy)-1,6-diazabicyclo[3.2.1]-octane-2-carbonitrile when crystallized from acetone.
Figure 2:
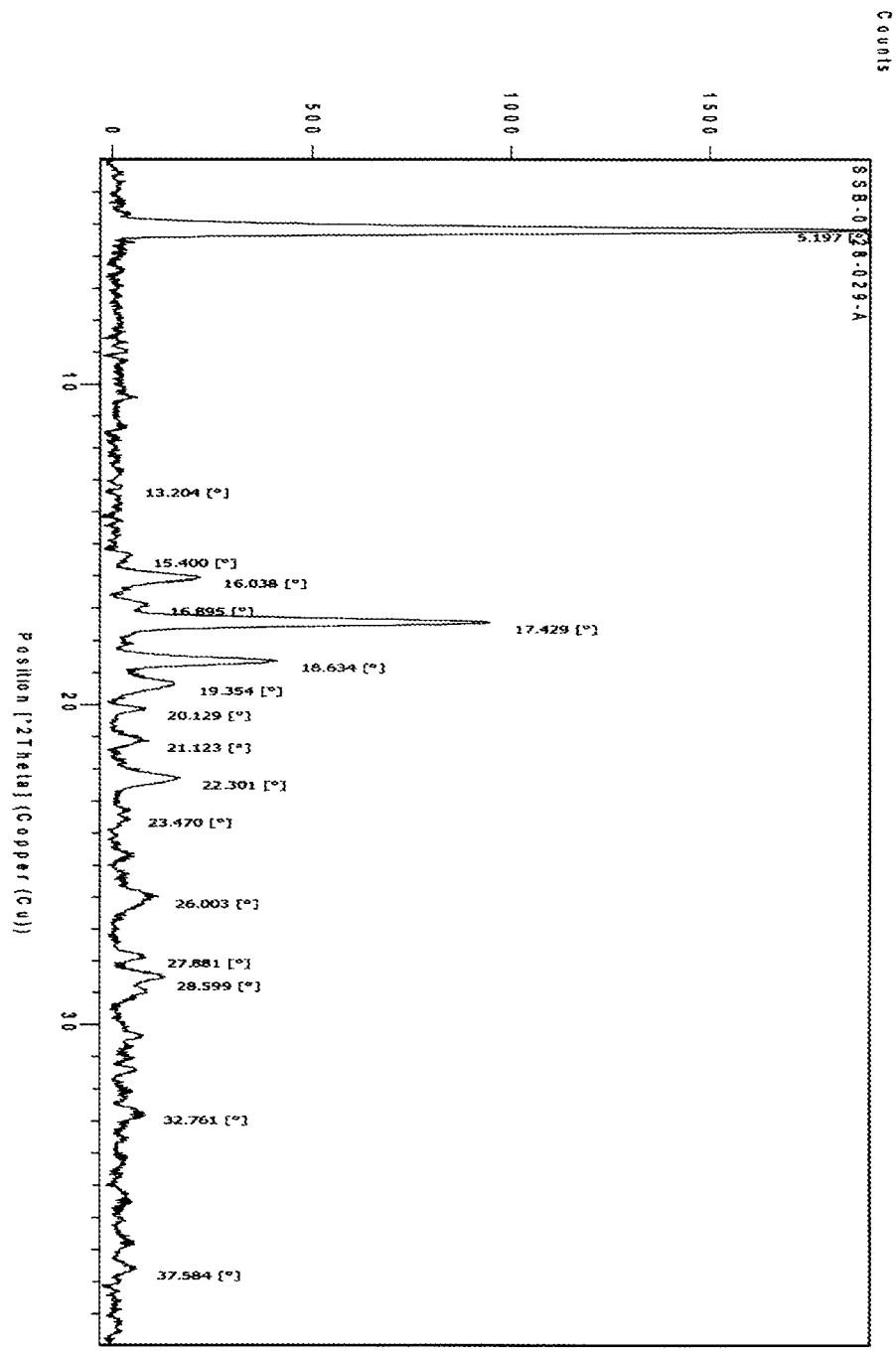
FIG. 2 is X-ray diffraction pattern of Polymorph II of Sodium salt of trans-7-oxo-6-(sulphoxy)-1,6-diazabicyclo[3.2.1]-octane-2-carbonitrile when crystallized from ethanol.
Figure 3:
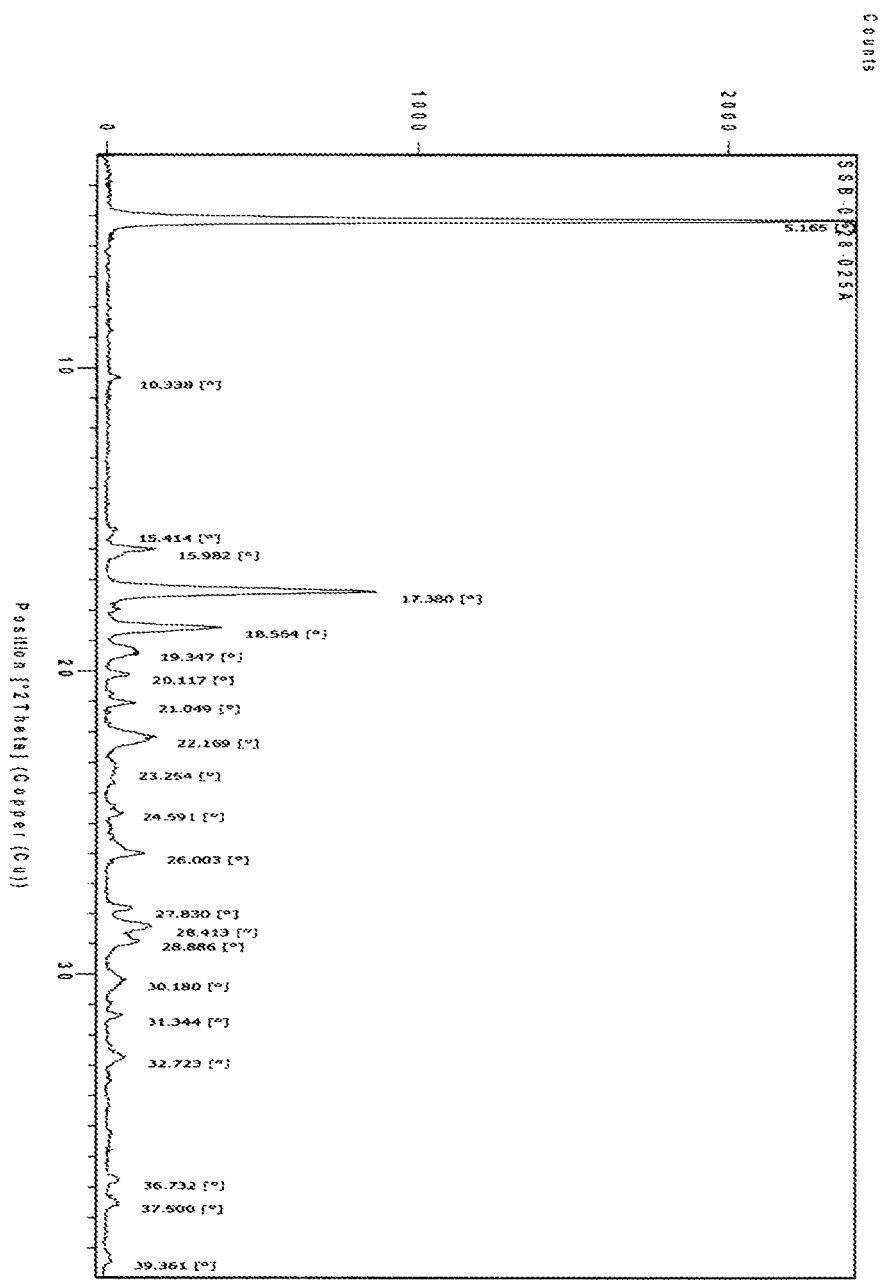
FIG. 3 is X-ray diffraction pattern of Polymorph III of Sodium salt of trans-7-oxo-6-(sulphoxy)-1,6-diazabicyclo[3.2.1]-octane-2-carbonitrile when crystallized from water.
Figure 4:
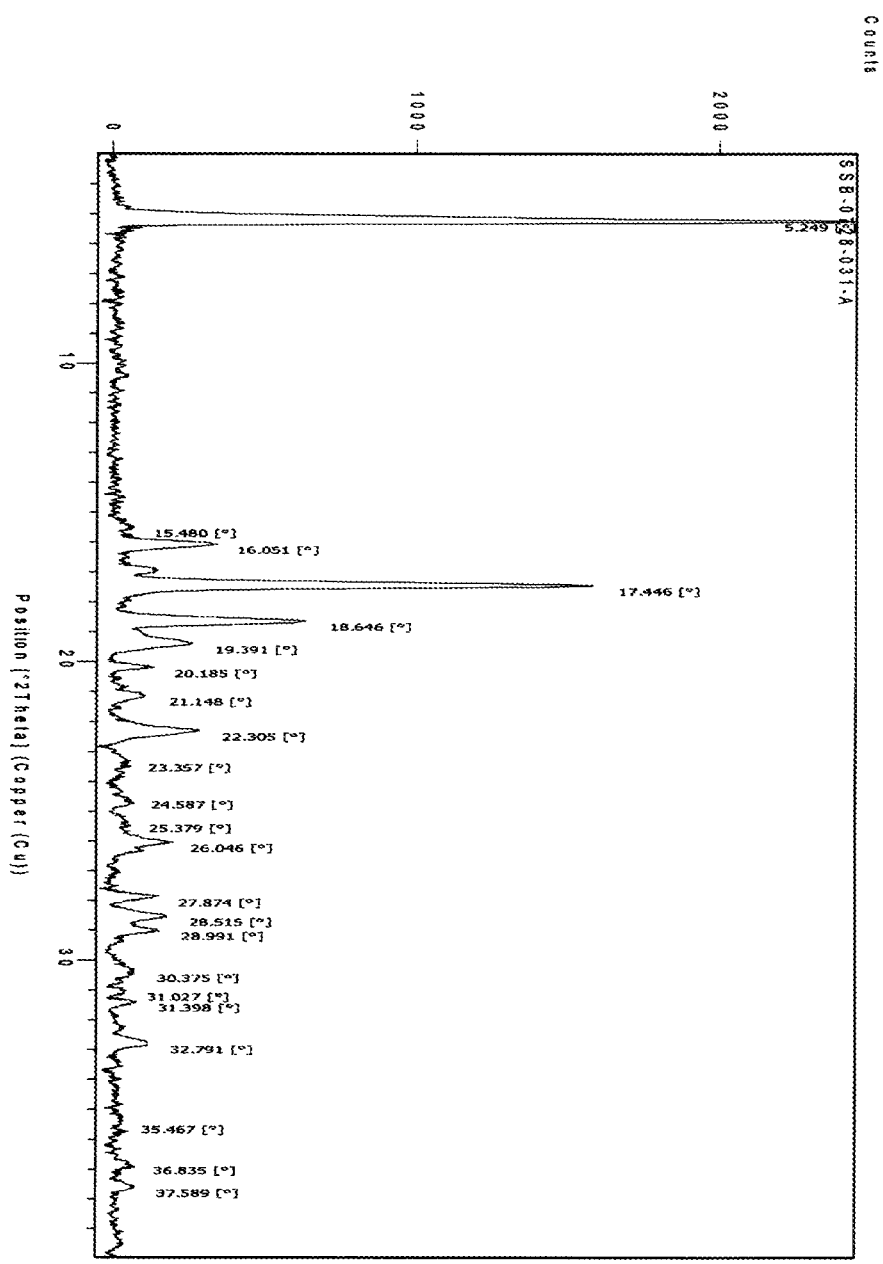
FIG. 4 is X-ray diffraction pattern of Polymorph IV of Sodium salt of trans-7-oxo-6-(sulphoxy)-1,6-diazabicyclo[3.2.1]-octane-2-carbonitrile when crystallized from acetonitrile.
Figure 5:
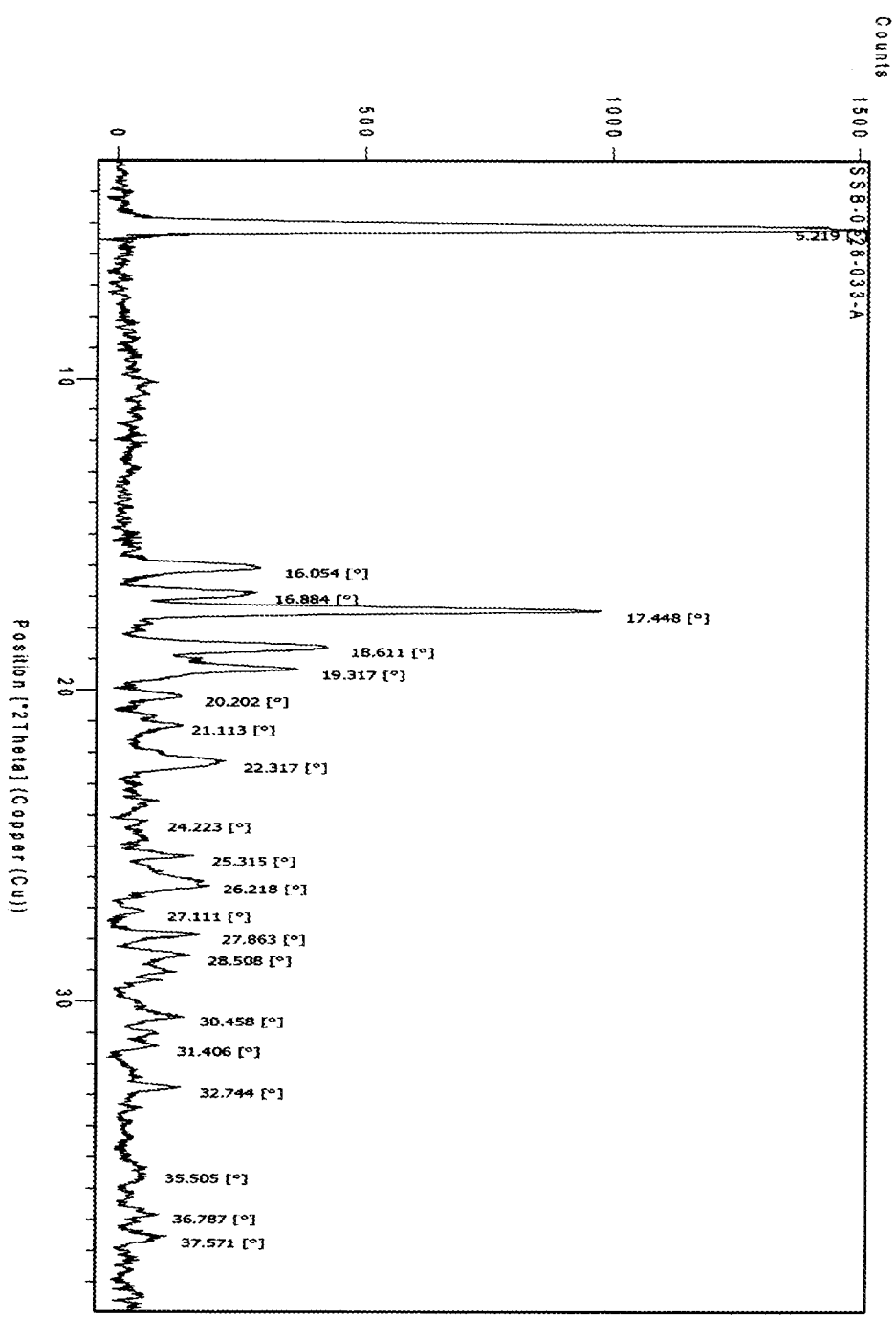
FIG. 5 is X-ray diffraction pattern of Polymorph V of Sodium salt of trans-7-oxo-6-(sulphoxy)-1,6-diazabicyclo[3.2.1]-octane-2-carbonitrile when crystallized from toluene.
Figure 6:
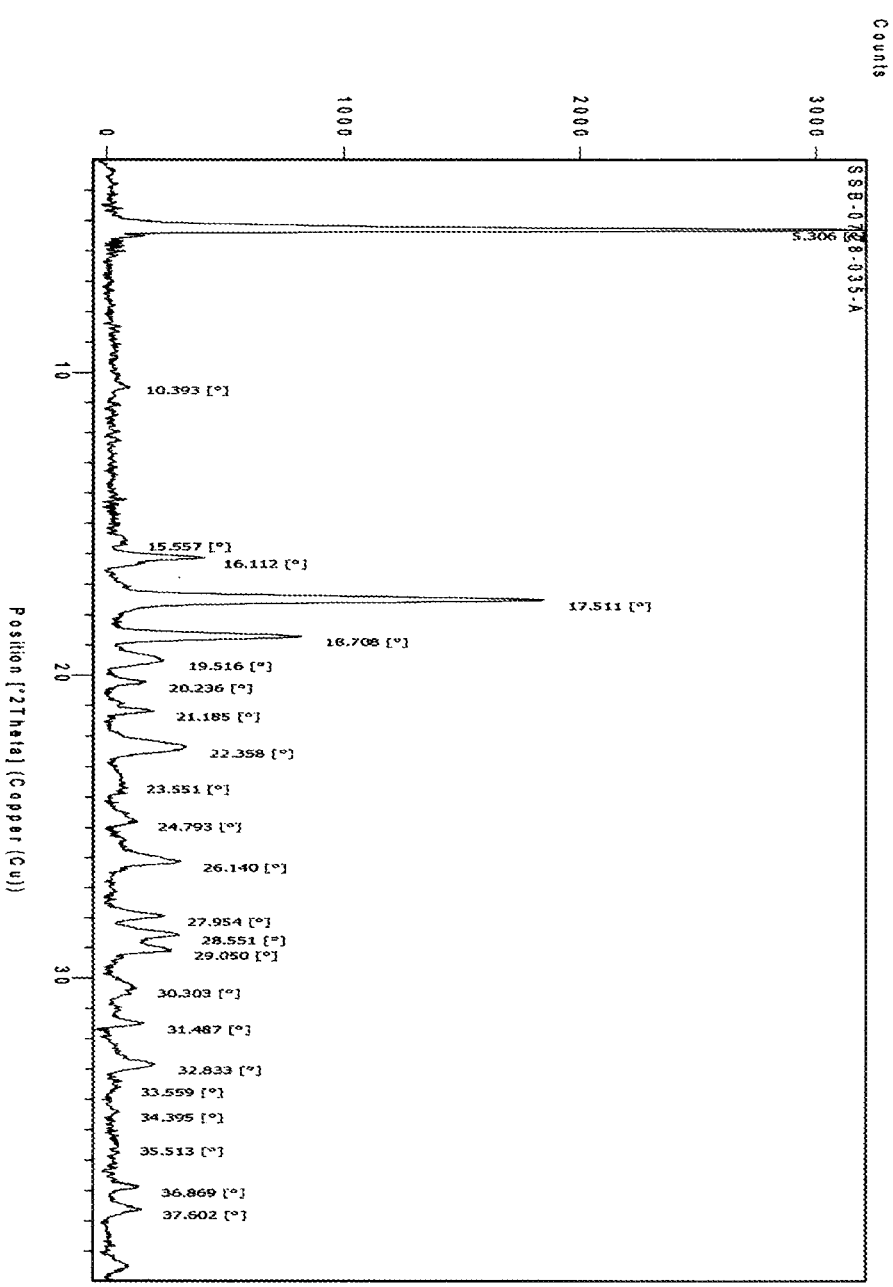
FIG. 6 is X-ray diffraction pattern of Polymorph VI of Sodium salt of trans-7-oxo-6-(sulphoxy)-1,6-diazabicyclo[3.2.1]-octane-2-carbonitrile when crystallized from tetrahydrofuran.

The biological activity of representative compounds of the invention against various bacterial strains (in combination with another antibacterial agent) was investigated. In a typical study, overnight grown bacterial cultures were diluted appropriately and inoculated on the agar media containing doubling dilutions of the antibiotics. Observation for growth or no growth was performed after 16-20 hours of incubation at 35±2° C. in ambient air. The overall procedure was performed as per Clinical and Laboratory Standards Institute (CLSI) recommendations (Clinical and Laboratory Standards Institute (CLSI), performance Standards for Antimicrobial Susceptibility Testing, 20th Informational Supplement, M 100-S20, Volume 30, No. 1, 2010). The results of these studies are summarized in Tables 1 and 2. Table 1 details potencies of ceftazidime in combination of representative compound according to the invention (compound of formula (I) wherein M is sodium) against various MDR (Multi Drug Resistant) Gram-negative strains producing Class A, C and D beta-lactamase enzymes. The activities are expressed as MICs (mcg/ml). For comparison, the activity of various other known beta-lactamase inhibitors such as clavulanic acid, tazobactam, MK-7655, and NXL-104 are also provided. As can be seen, the use of compounds according to the invention significantly lowered the MIC values of the antibacterial agent (e.g. in this case Ceftazidime). The results also suggest the compounds according the invention increase antibacterial effectiveness of an antibacterial agent when said antibacterial agent is co-administered with a pharmaceutically effective amount of a compound of Formula (I) or a stereoisomer or a pharmaceutically acceptable salt thereof.

TABLE 1

Comparative activity of compound of Formula (I) (wherein M is sodium) against Class A, Class C and Class D ESBL producing strains in combination with Ceftazidime

| ESBL Type | Strains | MICs in mcg/ml Ceftazidime | | | | |
|---|---|---|---|---|---|---|
| | | Control | + Clavulanic acid | + Tazobactam | + MK 7655 | + NXL104 | + Sodium salt of trans-7-oxo-6-(sulphoxy)-1,6-diazabicyclo[3.2.1]-octane-2-carbonitrile |
| Class A ESBL | K. pneumoniae ATCC 700603 | 32 | 0.5 | 1 | 2 | 0.5 | 0.5 |
| | E. coli NCTC 13351 | 32 | 0.5 | 0.5 | 2 | 0.5 | 0.5 |

TABLE 1-continued

Comparative activity of compound of Formula (I) (wherein M is sodium) against Class A, Class C and Class D ESBL producing strains in combination with Ceftazidime

| | | MICs in mcg/ml Ceftazidime | | | | | |
|---|---|---|---|---|---|---|---|
| ESBL Type | Strains | Control | + Clavulanic acid | + Tazobactam | + MK 7655 | + NXL104 | + Sodium salt of trans-7-oxo-6-(sulphoxy)-1,6-diazabicyclo[3.2.1]-octane-2-carbonitrile |
| | E.coli NCTC 13352 | >32 | 0.5 | 1 | 8 | 0.5 | 0.5 |
| Class C ESBL | E. coli M 50 | >32 | >32 | >32 | 2 | 1 | 1 |
| | E.coli 7 MP | >32 | >32 | >32 | 8 | 4 | 2 |
| | E.coli B 89 | >32 | >32 | >32 | 4 | 1 | 1 |
| Class D ESBL | A.baumanni NCTC 13301 | >32 | >32 | >32 | >32 | >32 | 32 |
| | A.baumanni NCTC 13304 | >32 | >32 | >32 | 32 | 32 | 32 |
| | A.baumanni NCTC 13305 | 16 | 16 | 16 | 16 | 16 | 16 |

All the inhibitors were tested at 4 mcg/ml at which they did not show their own, stand alone antibacterial activity Table 2 details data corresponding to a combination of Meropenem with a compound of Formula (I), wherein M is sodium, against Class D ESBL producing strains. Class D ESBLs producing pathogens that confer a high degree of resistance to carbapenems are a therapeutic problem in the clinical settings since extremely limited treatment options are available to treat them. As can be seen, the use of compounds according to the invention significantly lowered the MIC values of the antibacterial agent (e.g. in this case Meropenem). The results also suggest the compounds according the invention increase antibacterial effectiveness of an antibacterial agent when said antibacterial agent is co-administered with a pharmaceutically effective amount of a compound of Formula (I) or a stereoisomer or a pharmaceutically acceptable salt thereof.

TABLE 2

Comparative activity of WCK 4234 against Class D ESBL producing strains in combination with Meropenem

| | | MICs in mcg/ml Meropenem | | | | | |
|---|---|---|---|---|---|---|---|
| ESBL Type | Strains | Control | + Clavulanic acid | + Tazobactam | + MK 7655 | + NXL 104 | + Sodium salt of trans-7-oxo-6-(sulphoxy)-1,6-diazabicyclo[3.2.1]-octane-2-carbonitrile |
| Class D ESBL | A.baumanni NCTC 13301 | 32 | 32 | 32 | 32 | 16 | 4 |
| | A.baumanni NCTC 13304 | 32 | 32 | 32 | 32 | 16 | 2 |
| | A.baumanni NCTC 13305 | 8 | 8 | 8 | 8 | 8 | 2 |

All the inhibitors were tested at 4 mcg/ml at which they did not show their own, stand alone antibacterial activity

The invention claimed is:

1. A pharmaceutical composition comprising: (a) at least one antibacterial agent or a pharmaceutically acceptable salt thereof, and (b) a compound of Formula (I), or a stereoisomer or a pharmaceutically acceptable salt thereof; wherein M is a cation.

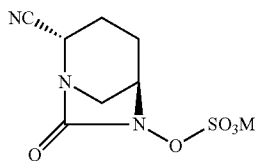

Formula (I)

2. A pharmaceutical composition according to claim 1, wherein the antibacterial agent is a beta-lactam antibacterial agent.

3. A pharmaceutical composition according to claim 1, wherein said antibacterial agent is selected from the group consisting of penicillins, penems, carbapenems, cephalosporins, and monobactams.

4. A pharmaceutical composition according to claim 1, wherein the antibacterial agent is a cephalosporin antibiotic selected from the group consisting of cephalothin, cephaloridine, cefaclor, cefadroxil, cefamandole, cefazolin, cephalexin, cephradine, ceftizoxime, cefoxitin, cephacetrile, cefotiam, cefotaxime, cefsulodin, cefoperazone, ceftizoxime, cefmenoxime, cefmetazole, cephaloglycin, cefonicid, cefodizime, cefpirome, ceftazidime, ceifriaxone, cefpiramide, cefbuperazone, cefozopran, cefepime, cefoselis, cefluprenam, cefuzonam, cefpimizole, cefclidin, cefixime, ceftibuten, cefdinir, cefpodoxime axetil, cefpodoxime proxetil, cefteram pivoxil, cefetamet pivoxil, cefcapene pivoxil or cefditoren pivoxil, cefuroxime, cefuroxime axetil, loracarbacef, ceftaroline, ceftolozane and latamoxef.

5. A pharmaceutical composition according to claim 1, wherein the antibacterial agent is selected from the group consisting of ceftazidime, cefepime, cefpirome, piperacillin, ertapenem, doripenem, meropenem, imipenem, ceftaroline and ceftolozane.

6. A method for treating bacterial infection in a subject, said method comprising administering to said subject a pharmaceutically effective amount of a pharmaceutical composition according to any one of the claims 1-5.

7. A method for treating bacterial infection in a subject, said method comprising administering to said subject a pharmaceutically effective amount of a pharmaceutical composition comprising a compound of Formula (I), or a stereoisomer or a pharmaceutically acceptable salt thereof; wherein M is a cation.

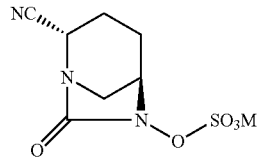

Formula (I)

8. A composition according to any one of the claims 1-5, wherein M is hydrogen, sodium or potassium.

9. A composition according to any one of the claims 6-7, wherein M is hydrogen, sodium or potassium.

* * * * *